US008962684B2

(12) United States Patent
Tojo et al.

(10) Patent No.: US 8,962,684 B2
(45) Date of Patent: Feb. 24, 2015

(54) ANTIOXIDANT COMPOSITION

(75) Inventors: Yosuke Tojo, Yokohama (JP); Chieko Mizumoto, Yokohama (JP); Yutaka Ashida, Yokohama (JP); Masashi Mita, Tokyo (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 13/261,240

(22) PCT Filed: Mar. 31, 2010

(86) PCT No.: PCT/JP2010/055842
§ 371 (c)(1),
(2), (4) Date: Mar. 28, 2012

(87) PCT Pub. No.: WO2011/040071
PCT Pub. Date: Apr. 7, 2011

(65) Prior Publication Data
US 2012/0184620 A1  Jul. 19, 2012

(30) Foreign Application Priority Data

Sep. 29, 2009 (JP) ................................ 2009-224742

(51) Int. Cl.
*A61K 31/195* (2006.01)
*A23L 1/305* (2006.01)
*A61K 8/44* (2006.01)
*A61K 31/198* (2006.01)
*A61K 45/06* (2006.01)
*A61Q 19/00* (2006.01)
*A61Q 19/08* (2006.01)

(52) U.S. Cl.
CPC ................. *A23L 1/3051* (2013.01); *A61K 8/44* (2013.01); *A61K 31/198* (2013.01); *A61K 45/06* (2013.01); *A61Q 19/007* (2013.01); *A61Q 19/08* (2013.01); *A23V 2002/00* (2013.01); *A61K 2800/522* (2013.01)
USPC ........................................................ 514/561

(58) Field of Classification Search
USPC ........................................................ 514/561
See application file for complete search history.

(56) References Cited

U.S. PATENT DOCUMENTS

2005/0250681 A1*  11/2005  Molina ............................ 514/9
2008/0234195 A1*   9/2008  Long et al. ...................... 514/12

FOREIGN PATENT DOCUMENTS

| EP | 2484340 A1 | 8/2012 |
| JP | 07-504810 A | 6/1995 |
| JP | 2005-003558 A | 1/2005 |
| JP | 2007-513104 A | 5/2007 |
| JP | 2007-517761 A | 7/2007 |
| JP | 2008-515770 A | 5/2008 |
| JP | 2008-185558 A | 8/2008 |
| JP | 2008-214250 A | 9/2008 |
| JP | 2009-526753 A | 7/2009 |
| KR | 10-2008-0071782 A | 8/2008 |
| WO | WO 90/13291 A1 | 11/1990 |
| WO | WO 93/10677 A1 | 6/1993 |
| WO | WO 94/15488 A2 | 7/1994 |
| WO | WO 95/03793 A1 | 2/1995 |
| WO | WO 02/96360 A2 | 12/2002 |
| WO | WO 2005/053680 A1 | 6/2005 |
| WO | WO 2005/065672 A1 | 7/2005 |
| WO | WO 2006/005455 A2 | 1/2006 |
| WO | WO 2007/079394 A2 | 7/2007 |
| WO | WO 2011/040363 A1 | 4/2011 |

OTHER PUBLICATIONS

Daxing et al, CN 1660063, published Aug. 31, 2005, abstract.*
Benesova et al (Journal of Separation Science, 2004, 27(4), 330-334).*
Peterson et al (227th ACS National Meeting Abstracts, 2004, CHED-486).*
Ahmed et al., "A new rapid and simple non-radioactive assay to monitor and determine the proliferation of lymphocytes: an alternative to [$^3$H]thymidine incorporation assay," Journal of Immunological Methods, 1994, 170:211-224.
Bickers et al., "Oxidative Stress in the Pathogenesis of Skin Disease," Journal of Investigative Dermatology, 2006, 126:2565-2575.
Chandrashekar et al., "Oxidative alterations induced by D-aspartic acid in prepubertal rat tesis in vitro: A mechanistic study," Theriogenology, 2008, 70:97-104.
Kajiro, Y., Ed., "Amino Acids," Harper's Biochemistry, $22^{nd}$ Edition, Maruzen Co. Ltd., Tokyo, Mar. 30, 1991, 21-30, with partial English translation of indicated portions, 2 pages.
Kinouchi et al., "D-Amino acid biosystem in mammal," Protein, Nucleic Acids and Enzymes, 2005, 50(5):453-460, with partial English translation of indicated portion, 1 page.
Maesato et al., "Cataract Model," Lens, Its Biochemical Mechanisms, S. Iwata, Ed., Medical-Aoi Publishing Co., Tokyo, Aug. 5, 1986, 318-323, with partial English translation of indicated portions, 2 pages.
Morikawa et al., "Alterations in D-amino acid levels in the brains of mice and rats after the administration of D-amino acids," Amino Acids, 2007, 32:13-20.
Yamashina et al., "Amino Acids, Peptides, and Proteins," Principles of Biochemistry, $2^{nd}$ Ed., Hirokawa Publishing Co., Tokyo, Apr. 15, 1993, 132-147, with partial English translation of indicated portion, 1 page.

(Continued)

*Primary Examiner* — Jason Sims
*Assistant Examiner* — Ibrahim D Bori
(74) *Attorney, Agent, or Firm* — Foley & Lardner LLP

(57) ABSTRACT

Disclosed is a stable and safe antioxidant composition which can be used routinely. Specifically disclosed is an antioxidant composition which contains one or more compounds selected from the group consisting of D-aspartic acid, derivatives and/or salts thereof. The composition may be used for the purpose of suppressing and/or improving skin conditions. The skin conditions may include, but is not limited to, fine wrinkles, a rough skin, a dry skin, a skin cancer, a skin allergy, an inflammation of the skin and a photosensitive dermatosis. The composition may be used for an external preparation for the skin, a food, and a pharmaceutical product for cataract.

5 Claims, 3 Drawing Sheets

(56) References Cited

OTHER PUBLICATIONS

Cui et al., "Protective action of honokiol, administered orally, against oxidative stress in brain of mice challenged with NMDA," Phytomedicine, 2007, 14:696-700.

Metoki et al., "Study of Effects of Antiglaucoma Eye Drops on N-Methyl-D-Aspartate-Induced Retinal Damage," Jpn. J. Ophthalmol., Nov. 1, 2005, 49(6):453-461.

Morikawa et al., "Alterations in D-amino acid levels in the brains of mice and rats after the administration of D-amino acids," Amino Acids, Jun. 7, 2006, 32(1):13-20.

* cited by examiner

ANTIOXIDANT COMPOSITION

CROSS-REFERENCE TO RELATED APPLICATIONS

This application is a National Stage application of PCT/JP2010/055842, filed Mar. 31, 2010, which claims priority from Japanese application JP 2009-224742, filed Sep. 29, 2009.

TECHNICAL FIELD

The present invention relates to an antioxidant composition which comprises one or more compounds selected from the group consisting of D-aspartic acid, derivatives and/or salts thereof, a method of improving a skin condition comprising a step of administering the compound, and a method of treating and/or preventing cataract comprising a step of administering the compound.

BACKGROUND ART

Reactive oxygen species (ROS) oxidize non-selectively bioactive biological substances like nucleic acids, proteins, and lipids to cause damages in function of a living body or structure of an organ and a tissue. ROS are known to be a cause of skin disorders like a skin cancer, a skin allergy, an inflammation of the skin, and a photosensitive dermatosis (Non-Patent Document 1). It is also known that, with an effect on the epidermis, they cause skin conditions like fine wrinkles, a rough skin, a dry skin and the like.

PRIOR ART DOCUMENTS

Non-Patent Document

Non-Patent Document 1: Bickers, D. R. and Athar, M., J., Invest Dermatolg., 126:2565 (2006)

DISCLOSURE OF THE INVENTION

Problem to be Solved by the Invention

As an antioxidant composition, ascorbic acid (vitamin C), α(alpha)-tocopherol (vitamin E) or the like has been conventionally used for a cosmetic product and a pharmaceutical product. However, the stability is not sufficient. And therefore, there is a need to develop a stable and safe antioxidant composition that can be used routinely.

Means for Solving the Problem

In this regard, the present invention provides an antioxidant composition comprising one or more compounds selected from the group consisting of D- and/or L-aspartic acid, derivatives and/or salts thereof.

The antioxidant composition of the present invention may be used for suppressing and/or improving a skin condition.

Regarding the antioxidant composition of the present invention, the skin condition comprises, but not limited thereto, fine wrinkles, a rough skin, a dry skin, a skin cancer, a skin allergy, an inflammation of the skin, and a photosensitive dermatosis.

The antioxidant composition of the present invention may be used for an external preparation for the skin.

The antioxidant composition of the present invention may be used for a food.

The antioxidant composition of the present invention may be used for a pharmaceutical product for cataract.

Regarding the antioxidant composition of the present invention, the pharmaceutical product for cataract may be a therapeutic agent for cataract or a prophylactic agent for cataract.

The antioxidant composition of the present invention may be used for an eye drop for cataract.

The cataract may be senile cataract.

The present invention provides a method of improving a skin condition comprising a step of administering an antioxidant composition comprised of one or more compounds selected from the group consisting of D- and/or L-aspartic acid, derivatives and/or salts thereof.

The skin condition that is suppressed and/or improved by the method of the present invention comprises, but not limited thereto, fine wrinkles, a rough skin, a dry skin, a skin cancer, a skin allergy, an inflammation of the skin, and a photosensitive dermatosis.

Regarding the method of the present invention, the antioxidant composition of the present invention may be used for an external preparation for the skin.

Regarding the method of the present invention, the antioxidant composition of the present invention may be used for a food composition.

The present invention also provides a method of treating and/or preventing cataract comprising a step of administering a composition comprised of one or more compounds selected from the group consisting of D- and/or L-aspartic acid, derivatives and/or salts thereof.

Regarding the method of treating and/or preventing cataract of the present invention, the pharmaceutical product for cataract may be an eye drop.

Regarding the method of treating and/or preventing cataract of the present invention, the cataract may be senile cataract.

As used in the present description, the term "salt" of aspartic acid indicates any salt comprising a metal salt and an amine salt and the like, provided that the antioxidant effect of aspartic acid is not impaired. The metal salt may comprise an alkaline metal salt, an alkaline earth metal salt and the like. The amine salt may comprise a triethylamine salt, a benzylamine salt and the like.

As used in the present description, the term "derivatives" of aspartic acid indicates an aspartic acid molecule that is covalently bound to any atomic group via its amino group, carboxyl group, or side chain, provided that the antioxidant effect of aspartic acid is not impaired. The atomic group comprises, but is not limited to, a protective group, such as N-phenylacetyl group, and 4,4'-dimethoxytrityl (DMT) group, a biopolymer, such as a protein, a peptide, a saccharide, a lipid, and a nucleic acid; a synthetic polymer, such as a polystyrene, a polyethylene, a polyvinyl, and a polyester; and a functional group such as an ester group. The ester group may comprise, for example, an aliphatic ester, such as methyl ester, and ethyl ester, and an aromatic ester.

An amino acid has optical isomers which are the L-form and D-form. A natural protein has L-amino acids bound by peptide bonds and only L-amino acids are employed excluding some exceptions such as a bacterial cell wall. Therefore, it has been considered that in a mammal including a human only L-amino acids are present and only L-amino acids are utilized (Kinouchi, T. et al., TANPAKUSHITSU KAKUSAN KOSO (PROTEIN, NUCLEIC ACID AND ENZYME), 50:453-460 (2005), Lehninger Principles of Biochemistry [Vol. 1] 2nd ed., pp 132-147 (1993), Japanese-language translation, Hirokawa Shoten Ltd., Harper's Biochemistry, Original version, 22nd ed., pp 21-30 (1991), Japanese-language translation Maruzen Co., Ltd.). Accordingly, only L-amino acids have been mostly employed as amino acids academically and industrially for a long time.

Exceptional cases where a D-amino acid is employed are, for example, a case of using as a raw material for an antibiotics produced by a microorganism, and, a case of a food additive employing a D-amino acid in a DL-amino acid mixture for the purpose of reducing cost of fractionating only an L-amino acid from a mixture of the L- and D-amino acids, which are obtained in equimolar amounts by synthesizing the amino acids. Nevertheless, there has been no case of using only D-amino acid industrially as a bioactive substance.

D-aspartic acid is found to be localized in the testis or the pineal body, and it is known to be involved in the control of hormone secretion (Japanese Patent Unexamined Publication No. 2005-3558). However, physiological activity of D-aspartic acid in the skin has not been clearly elucidated.

As shown in the following Examples, it has not been known that L- and D-aspartic acids can suppress oxidative damages so far. Thus, the antioxidant composition comprising L- and/or D-aspartic acid according to the present invention is a novel invention.

Recently, it was reported that ddY mice were allowed to ingest freely a 10 mM aqueous solution of a D-amino acid for two weeks and then examined for the D-amino acid concentration in each organ, which was 3 to 1000 pmol per gland in the pineal body and 2 to 500 nmol per wet gram in the brain tissue (Morikawa, A. et al., Amino Acids, 32:13-20 (2007)). Based on this, the lower limit for daily intake amount of L- and D-aspartic acids that are contained in the composition of the present invention is calculated as described below.

The aspartic acid of the present invention has an effect on suppressing oxidative damages in cultured human fibroblast cells at the concentrations of 0.1 $\mu$M (micro-molar) to 10 $\mu$M (micro-molar), as shown in the following examples. Thus, the amount of the aspartic acid that is contained in the agent for improving skin conditions, an external preparation for skin, and a food composition of the present invention may be any content, provided that the aspartic acid in the above concentration range is distributed to fibroblast cells in a skin tissue of a living organism. When the composition of the present invention is an external preparation, the content of the aspartic acid may be 0.000015% by weight to 50% by weight, or up to the maximum weight concentration that can be formulated, in the total composition of the present invention. Specifically, when the composition is an external preparation, the content of the aspartic acid is preferably 0.00003% by weight to 30% by weight, and the most preferably 0.0003% by weight to 3% by weight. When the composition of the present invention is an internal agent, the content of the aspartic acid may be 0.00001% by weight to 100% by weight. When the composition of the present invention is an internal agent, the content of the aspartic acid is preferably 0.00002% by weight to 80% by weight and the most preferably 0.0002% by weight to 60% by weight. Further, the lower limit of a daily intake amount of D-aspartic acid that is contained in the composition of the present invention may be 0.01 ng, preferably 0.1 ng, and more preferably 1 ng per 1 kg of body weight. The lower limit of a daily intake amount of L-aspartic acid that is contained in the composition of the present invention is an amount that is less than the general dose of commercially available medicines (20 mg per 1 kg of body weight), e.g., 0.01 mg, preferably 0.1 mg, and more preferably 1 mg per 1 kg of body weight.

The composition of the present invention may further comprise, in addition to the single body of aspartic acid, a salt of aspartic acid and/or a derivative capable of releasing aspartic acid by a drug metabolizing enzyme and the like in vivo, one or more pharmaceutically acceptable additives, provided that the antioxidative effect of aspartic acid on oxidative damages is not impaired. Such an additive comprises, but is not limited to, a diluent and an extender, a binder and an adhesive, a lubricant, a glidant, a plasticizer, a disintegrant, a carrier solvent, a buffering agent, a colorant, a flavoring agent, a sweetener, a preservative and a stabilizer, an adsorbent, as well as other pharmaceutical additives known to those skilled in the art.

The composition of the present invention may be prepared by only using, as an active ingredient, aspartic acid, salts of aspartic acid and/or derivatives capable of releasing aspartic acid by a drug metabolizing enzyme and the like in vivo. However, within the range that the effect on oxidative damages of the present invention is not impaired, it may be appropriately formulated with other components that are used for an external preparation for the skin like cosmetics including quasi drugs and pharmaceutical products, if necessary. Examples of other ingredients (i.e., optionally formulated ingredients) comprise an oil, a surface active agent, a powder, a colorant, water, alcohols, a thickening agent, a chelating agent, silicones, an antioxidant, an UV absorbing agent, a moisturizing agent, a flavoring agent, various pharmaceutically active ingredients, a preservative, a pH adjusting agent, and a neutralizing agent.

A dosage form of an antioxidant composition of the present invention that is used for suppressing and/or improving skin conditions (herein below, referred to as an "agent for improving skin conditions") may be any one that is commonly used for a quasi drug composition and a pharmaceutical composition comprising an external preparation for skin like an ointment, a cream, an emulsion, a lotion, a pack, gel, and a patch; and an oral preparation like a powder, granules, a soft capsule, and a tablet; a nasal preparation like a nasal spray; and an injection solution.

A dosage form of the external preparation for the skin according to the present invention is not specifically limited, provided that it is conventionally used for an external preparation for the skin, and it comprises an ointment, a cream, an emulsion, a lotion, a pack, a gel, and a patch.

The food composition of the present invention may further comprise, in addition to aspartic acid, salts of aspartic acid and/or derivatives capable of releasing aspartic acid by a drug metabolizing enzyme and the like in vivo, a flavoring agent, a colorant, a preservative, and other components that can be used for a food product, provided that the effect of aspartic acid on oxidative damages is not impaired.

The food composition of the present invention may be any one employed conventionally as a food composition comprising, but not limited to, a candy, a cookie, bean paste, a French dressing, a mayonnaise, a French bread, a soy sauce, yogurt, dried seasoning powder for rice, seasoning sauce/sauce for natto (Japanese fermented soybean), natto, unrefined black vinegar.

ROS are known to cause not only skin disorders but also cataract. They are believed not only to disturb lipid constitution by producing lipid peroxides to polyunsaturated fatty acids inside crystalline lens via reduction of hydrogen peroxide and free radical chain reactions, but also to impair the membrane function by denaturing proteins eventually causing opacity of the lens. ("SUISHOTAI SONO SEIKA-GAKUTEKI KIKO (BIOCHEMICAL MECHANISM OF CRYSTALLINE LENS", pp 318-323, by Maesato Takami and Iwata Shuzo, edited by Iwata Shuzo, published by Medical-Aoi Publications, Inc., Tokyo (1986)). According to the findings above and the Examples described below, D- and/or L-aspartic acid having an antioxidant activity is effective for prophylaxis or treatment of cataract.

DESCRIPTION OF EMBODIMENTS

Figure 1:
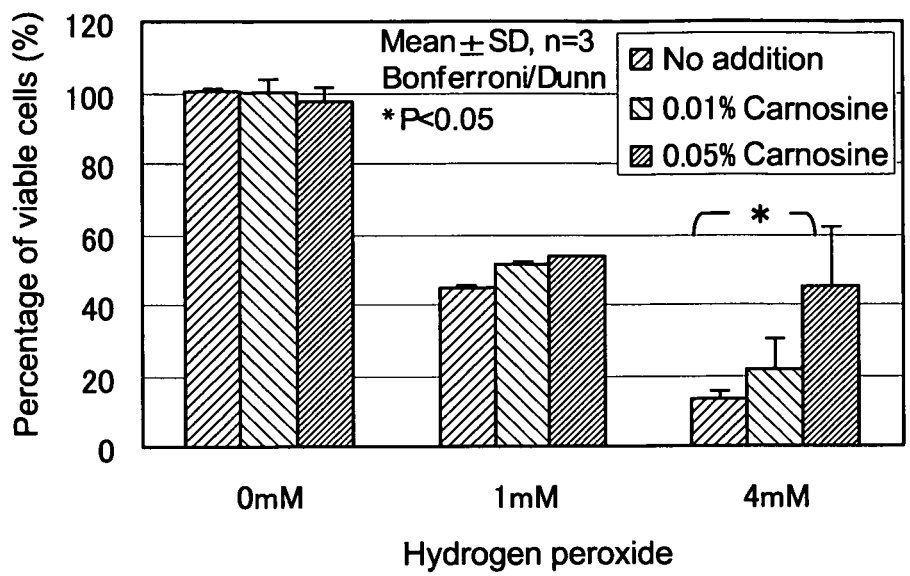
FIG. 1 is a graph showing the effect of carnosine on oxidative damages induced by hydrogen peroxide in normal human skin fibroblast cells.

Examples of the present invention described below are intended only to exemplify the present invention rather than to limit the technical scope thereof. The technical scope of the present invention is limited only by the description in claims.

Example 1

Experiment for Evaluation of Antioxidant Effect

1. Object

ROS include reactive oxygen species in the narrow sense comprising superoxide anion, hydroxyl radical, hydroperoxide and singlet oxygen, and reactive oxygen species in the broad sense comprising an alkoxy radical, hydroperoxyl radical, a peroxyl radical, hydroperoxide, and a transition metal-oxygen complex and the like. Among the ROS, hydroxyl radical has the most potent oxidizing activity, but has very short lifetime. As such, it oxidizes non-selectively body components like nucleic acids, proteins, and lipids that are present in the vicinity of their generation site. However, peroxyl radical has a weak oxidizing activity but is relatively stable. As such, it can diffuse and cause a cell membrane damage via free radical chain reactions of polyunsaturated fatty acids. Meanwhile, hydroxyl radical generates a peroxyl radical but no hydroxyl radical is generated from a peroxyl radical. Since the working mechanism is different between a hydroxyl radical and a peroxyl radical, an effective antioxidant may be also different for each of them. For such reasons, in the present examples, an antioxidant effect was evaluated for both hydrogen peroxide and 2,2'-azobis (2-amidinopropane) dihydrochloride salt (herein below, referred to as "AAPH"), that are the representative examples of a compound which can generate hydroxyl radical and a peroxyl radical, respectively. As a positive control, carnosine having a known antioxidant activity was used.

2. Materials and Methods 2-1. Cells

For the evaluation of an antioxidant effect on hydrogen peroxide, human neonatal skin fibroblast cells (trade name: Cryo NHDF-Neo, manufactured by Sankyo Junyaku Co., Ltd.) were inoculated to a 24-well plate to have $1\times10^5$ cells per well. The cells were then cultured for four hours in a medium for cell culture (trade name: D-MEM (1 g/L glucose), manufactured by Wako Pure Chemical Industries) supplemented with 10% bovine fetal serum (herein below, referred to as a "standard medium") in a 5% $CO_2$ and saturated water vapor atmosphere at 37° C. (degrees Celsius). For the evaluation of an antioxidant effect on AAPH, antibiotics (penicillin, streptomycin, and fungizone) were supplemented to the standard medium and the cells were cultured for one day.

2-2. Medium for Evaluation of Antioxidant Effect

Subsequently, the culture medium was switched to a medium for cell culture (trade name: D-MEM (1 g/L glucose), manufactured by Wako Pure Chemicals Industries) supplemented with 0.5% bovine fetal serum (herein below, referred to as "low-serum medium") to which 0.01% or 0.05% carnosine, or 0.1 µM (micro-molar) or 10 µM (micro-molar) D- or L-aspartic acid had been added, and the cells were cultured for two days under atmosphere of 5% $CO_2$ and saturated moisture at 37° C. (degrees Celsius). For the experiment for the evaluation of oxidative damages on AAPH, the culture medium was switched to the medium for cell culture to which 5 ppm or 100 ppm carnosine, or 10 µM (micro-molar) D- or L-aspartic acid had been further added, and the cells were cultured for two days. The low-serum medium described above to which neither carnosine nor aspartic acid had been added was employed as a negative control.

2-3. Addition of Oxidant

After culturing for two days, 1 mM or 4 mM hydrogen peroxide, or 50 mM or 100 mM AAPH was added to the medium for evaluating an antioxidant effect, and the antioxidant effect was evaluated for carnosine or aspartic acid. The low-serum medium described above to which neither hydrogen peroxide nor AAPH had been added was employed as a control for evaluation of toxicity of an antioxidant when no oxidant was added.

2-4. Quantification of Oxidative Damages

Two hours after the addition of hydrogen peroxide or AAPH, AlarmarBlue (trade name: Biosource, manufactured by Biosource International Inc.) was added to have final concentration of 10%. Two to three hours later, according to the methods by Ahmed S. A. et al. (J. Immunol. Method., 170, 211-224 (1994)) and the instructions provided by the manufacturer, the fluorescent intensity of the supernatant was measured with an excitation wavelength of 544 nm, and an emission wavelength of 590 nm.

3. Results 3-1. Antioxidant Effect of Carnosine on Hydrogen Peroxide

FIG. 1 shows the results of the experiment obtained by examining the antioxidant effect of carnosine on hydrogen peroxide in Cryo NHDF-Neo cells. The error bars for each experimental condition indicate the standard deviations of the experimentally measured values obtained by repeating the experiment three times under the identical condition. The asterisk (*) indicates that t is less than 5% by Bonferroni/Dunn test.

The ratio of viable cells for the control group for evaluating toxicity of the antioxidant without addition of an oxidant was 102% when carnosine had not been added. When the concentration of carnosine was 0.01%, it was 100%. When the concentration of carnosine was 0.05%, it was 97%. The ratio of viable cells in the case of addition of 1 mM hydrogen peroxide was 45% when carnosine had not been added. When the concentration of carnosine was 0.01%, it was 51%. When the concentration of carnosine was 0.05%, it was 53%. The ratio of viable cells in the case of 4 mM hydrogen peroxide was 14% when carnosine had not been added. When the concentration of carnosine was 0.01%, it was 21%. When the concentration of carnosine was 0.05%, it was 45%. Thus, when the concentration of hydrogen peroxide was 4 mM, a significant difference in the ratio of viable cells was observed for the case in which 0.05% carnosine had been added compared to the ratio without addition of carnosine. Based on the results above, the antioxidant effect of carnosine on hydrogen peroxide was confirmed in the experiment system of the present example.

3-2. Antioxidant Effect of L-Aspartic Acid on Hydrogen Peroxide

Figure 2:
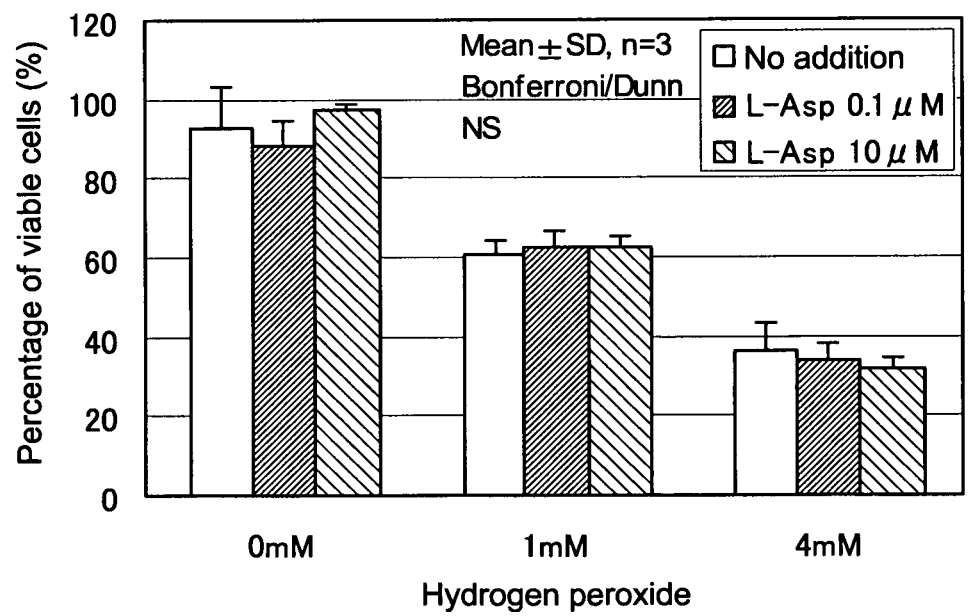
FIG. 2 is a graph showing the effect of L-aspartic acid on oxidative damages induced by hydrogen peroxide in normal human skin fibroblast cells.

FIG. 2 shows the results of the experiment obtained by examining the antioxidant effect of L-aspartic acid on hydrogen peroxide in Cryo NHDF-Neo cells. The error bars for each experimental condition indicate the standard deviations of experimentally measured values obtained by repeating the experiment three times under the identical condition.

The ratio of viable cells for the control group for evaluating toxicity of an antioxidant without addition of an oxidant was 93% when L-aspartic acid had not been added. When the concentration of L-aspartic acid was 0.1 µl (micro-molar), it was 88%. When the concentration of L-aspartic acid was 10 µM (micro-molar), it was 97%. The ratio of viable cells in the case of 1 mM hydrogen peroxide was 61% when L-aspartic acid had not been added. When the concentration of L-aspartic acid was 0.1 µM (micro-molar), it was 62%. When the concentration of L-aspartic acid was 10 µM (micro-molar), it was 62%. The ratio of viable cells in the case of 4 mM hydrogen peroxide was 36% when L-aspartic acid had not been added. When the concentration of L-aspartic acid was 0.1 µM (micro-molar), it was 33%. When the concentration of L-aspartic acid was 10 µM (micro-molar), it was 32%. Based on the results above, a statistically significant antioxidant effect of L-aspartic acid on hydrogen peroxide was not observed.

3-3. Antioxidant Effect of D-Aspartic Acid on Hydrogen Peroxide

Figure 3:
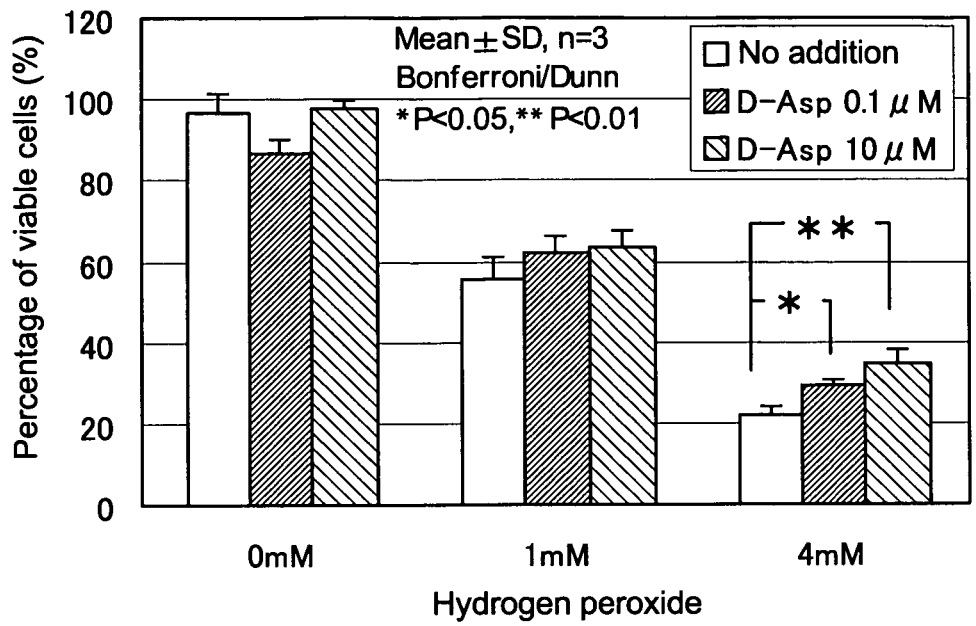
FIG. 3 is a graph showing the effect of D-aspartic acid on oxidative damages induced by hydrogen peroxide in normal human skin fibroblast cells.

FIG. 3 shows the results of the experiment obtained by examining the antioxidant effect of D-aspartic acid on oxidative damages induced by hydrogen peroxide in Cryo NHDF-Neo cells. The error bars for each experimental condition indicate the standard deviations of experimentally measured values obtained by repeating the experiment three times under the identical condition. The asterisk (*) indicates that p is less than 5% by Bonferroni/Dunn test. The double asterisk (**) indicates that p is less than 1% by Bonferroni/Dunn test.

The ratio of viable cells for the control group for evaluating toxicity of an antioxidant without addition of an oxidant was 97% when D-aspartic acid had not been added. When the concentration of D-aspartic acid was 0.1 µM (micro-molar), it was 86%. When the concentration of D-aspartic acid was 10 µM (micro-molar), it was 97%. In the case of 1 mM hydrogen peroxide, the ratio of viable cells was 55% when D-aspartic acid had not been added. When the concentration of D-aspartic acid was 0.1 µM (micro-molar), it was 62%. When the concentration of D-aspartic acid was 10 µM (micro-molar), it was 63%. In the case of 4 mM hydrogen peroxide, the ratio of viable cells was 22% when D-aspartic acid had not been added. When the concentration of D-aspartic acid was 0.1 µM (micro-molar), it was 29%. When the concentration of D-aspartic acid was 10 µM (micro-molar), it was 34%. Thus, when the concentration of hydrogen peroxide was 4 mM, a significant difference in the ratio of viable cells was observed for the case in which 0.1 µM (micro-molar) or 10 µM (micro-molar) D-aspartic acid had been added compared to the ratio without addition of D-aspartic acid. Based on the results above, the concentration-dependent antioxidant effect of D-aspartic acid on hydrogen peroxide was observed.

Figure 4:
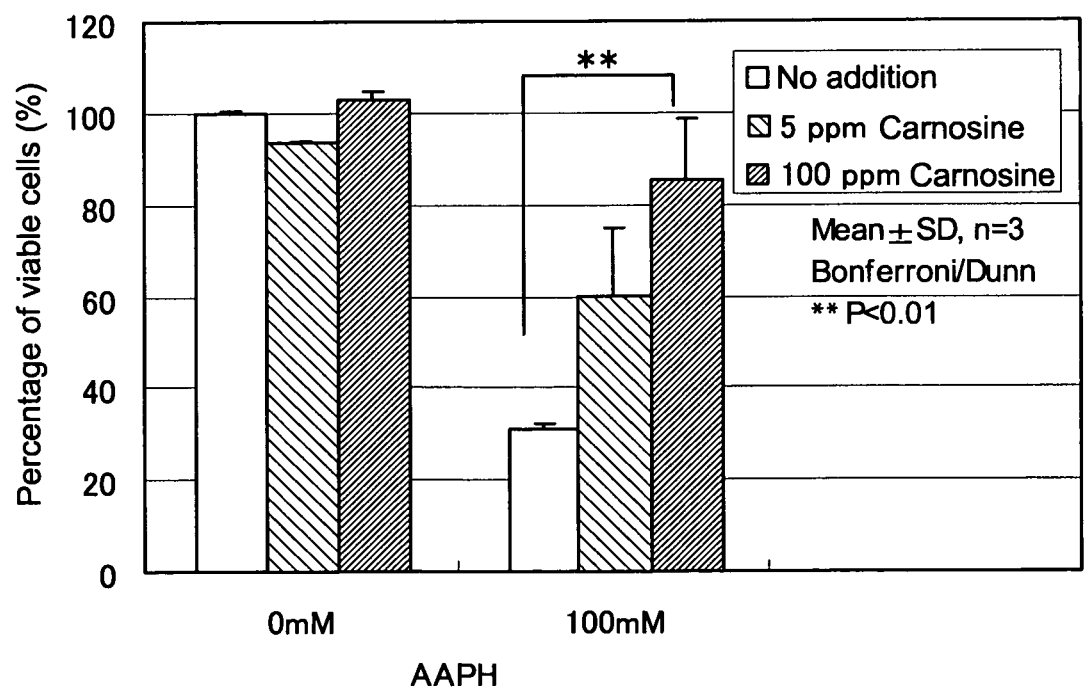
FIG. 4 is a graph showing the effect of carnosine on oxidative damages by AAPH in normal human skin fibroblast cells.

3-4. Antioxidant Effect of Carnosine in Experiment for Evaluating Oxidative Damages Induced by AAPH FIG. 4 shows the experiment obtained by examining the antioxidant effect of carnosine in the experiment for evaluating oxidative damages induced by AAPH in Cryo NHDF-Neo cells. The error bars for each experimental condition indicate the standard deviations of experimentally measured values obtained by repeating the experiment three times under the identical condition. The double asterisk (**) indicates that p is less than 1% by Bonferroni/Dunn test.

The ratio of viable cells for the control group for evaluating toxicity of an antioxidant without addition of an oxidant was 100% when carnosine had not been added. When the concentration of carnosine was 5 ppm, it was 93%. When the concentration of carnosine was 100 ppm, it was 103%. The ratio of viable cells in the case of 100 mM AAPH was 31% when carnosine had not been added. When the concentration of carnosine was 5 ppm, it was 60%. When the concentration of carnosine was 100 ppm, it was 85%. When AAPH had concentration of 100 mM, a significant difference was observed for the ratio of viable cells for the case in which carnosine had been added at the concentration of 100 ppm compared to the ratio without addition of carnosine. Based on the results above, the antioxidant effect of carnosine on AAPH was confirmed by the experiment system of the present example.

Figure 5:
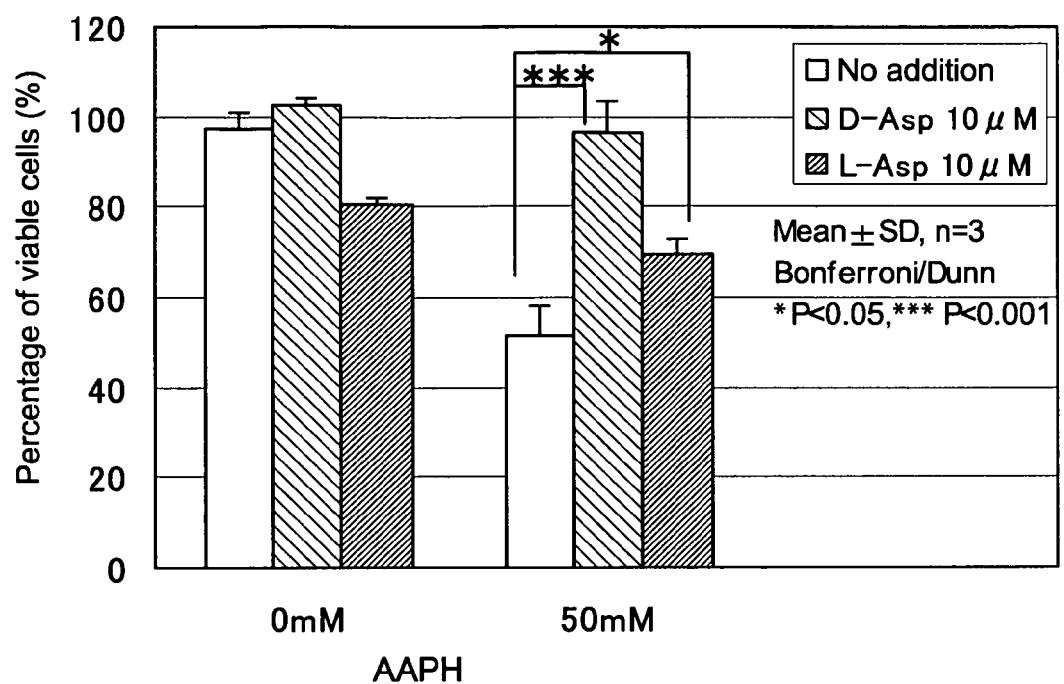
FIG. 5 is a graph showing the effect of L- and D-aspartic acids on oxidative damages induced by AAPH in normal human skin fibroblast cells.

3-5. Antioxidant Effect of L- and D-Aspartic Acids in Experiment for Evaluating Oxidative Damages Induced by AAPH FIG. 5 shows the experiment obtained by examining the antioxidant effect of L- and D-aspartic acids in the experiment for evaluating oxidative damages induced by AAPH in Cryo NHDF-Neo cells. The error bars for each experimental condition indicate the standard deviations of the experimentally measured values obtained by repeating the test three times under the identical condition. The asterisk (*) indicates that p is less than 5% by Bonferroni/Dunn test. The triple asterisk (***) indicates that p is less than 0.1% by Bonferroni/Dunn test.

The ratio of viable cells for the control group for evaluating toxicity of an antioxidant without addition of the oxidant was 95% when L- and D-aspartic acids had not been added. When the concentration of D-aspartic acid was 10 µM (micro-molar), it was 102%. When the concentration of L-aspartic acid was 10 µM (micro-molar), it was 80%. In the case of 100 mM AAPH, the ratio of viable cells was 51% when L- and D-aspartic acids had not been added. When the concentration of D-aspartic acid was 10 µM (micro-molar), it was 96%. When the concentration of L-aspartic acid was 10 µM (micro-molar), it was 69%. When AAPH had concentration of 100 mM, a significant difference was observed for the ratio of viable cells for the case in which L- and D-aspartic acids had been added at concentration of 10 µM (micro-molar) compared to the ratio without addition of L- and D-aspartic acids. Based on the results above, it was indicated that D-aspartic acid had more potent antioxidant effect on AAPH compared to L-aspartic acid.

4. Conclusions

Based on the experimental results of the Examples above, D-aspartic acid was found to have an antioxidant effect on both hydrogen peroxide and AAPH. However, L-aspartic acid was found to have an antioxidant effect on AAPH only. Thus, it was indicated that D-aspartic acid is effective against both hydroxyl radical and a peroxyl radical, but L-aspartic acid is effective only against a peroxyl radical.

Example 2

Formulation examples of a composition comprising aspartic acid according to the present invention, i.e., an emulsion preparation, a patch, a tablet, a soft capsule, a granule, a beverage, a candy, a cookie, bean paste, a French dressing, a mayonnaise, a French bread, a soy sauce, yogurt, dried seasoning powder for rice, seasoning/sauce for natto, natto, unrefined black vinegar, cream, body cream, gel, a peel-off mask, a wet pack, an emulsion, a skin lotion, and an aerosol preparation, are given below. The aspartic acid in the formulation examples is either D-form and/or L-form.

These formulation examples are all illustrative and not intended to limit the technical scope of the present invention.

Formulation Example 1

Emulsion Preparation

| (Composition) | Content (% by weight) |
| --- | --- |
| Aspartic acid | 0.42 |
| Behenyl alcohol | 0.2 |
| Cetanol | 0.5 |
| Glycerin monofatty acid ester | 1.8 |
| Hydrogenated castor oil POE (60) | 1.0 |
| White petrolatum | 2.0 |
| Liquid paraffin | 10.0 |
| Isopropyl myristate | 3.0 |
| Methyl polysiloxane (6cs) | 1.5 |
| Concentrated glycerin | 13.0 |
| Dipropylene glycol | 2.0 |
| Carboxyvinyl polymer | 0.25 |
| Sodium hyaluronate | 0.005 |
| Potassium hydroxide | Proper quantity |
| Lactic acid | Proper quantity |
| Edetate sodium | Proper quantity |
| Ethylparaben | Proper quantity |
| Purified water | Remainder |
| | 100.000 |

Formulation Example 2

Patch

| (Composition) | Content (% by weight) |
| --- | --- |
| Aspartic acid | 0.3 |
| Polyacrylic acid | 3.0 |
| Sodium polyacrylate | 2.5 |
| Gelatin | 0.5 |
| Sodium carboxymethyl cellulose | 4.0 |
| Polyvinyl alcohol | 0.3 |
| Concentrated glycerin | 14.0 |
| 1,3-Butylene glycol | 12.0 |
| Aluminum hydroxide | 0.1 |
| Edetate sodium | 0.03 |
| Methylparaben | 0.1 |
| Purified water | Remainder |
| | 100.00 |

Formulation Example 3

Tablet

| (Composition) | Content (mg/tablet) |
| --- | --- |
| Aspartic acid | 360.5 |
| Lactose | 102.4 |
| Calcium carboxymethyl cellulose | 29.9 |
| Hydroxypropyl cellulose | 6.8 |
| Magnesium stearate | 5.2 |
| Crystalline cellulose | 10.2 |
| | 515.0 |

Formulation Example 4

Tablet

| (Composition) | Content (mg/tablet) |
| --- | --- |
| Sucrose ester | 70 |
| Crystalline cellulose | 74 |
| Methyl cellulose | 36 |
| Glycerin | 25 |
| Aspartic acid | 475 |
| N-Acetylglucosamine | 200 |
| Hyaluronic acid | 150 |
| Vitamin E | 30 |
| Vitamin B6 | 20 |
| Vitamin B2 | 10 |
| α(alpha)-Lipoic acid | 20 |
| Coenzyme Q10 | 40 |
| Ceramide (*Konjac* extract) | 50 |
| L-Proline | 300 |
| | 1500 |

Formulation Example 5

Soft Capsule

| (Composition) | Content (mg/capsule) |
| --- | --- |
| Edible soybean oil | 530 |
| *Eucommia ulmoides* extract | 50 |
| Ginseng extract | 50 |
| Aspartic acid | 100 |
| Royal jelly | 50 |
| Maca | 30 |
| GABA | 30 |
| Beeswax | 60 |
| Gelatin | 375 |
| Glycerin | 120 |
| Glycerin fatty acid ester | 105 |
| | 1500 |

Formulation Example 6

Soft Capsule

| (Composition) | Content (mg/capsule) |
| --- | --- |
| Brown rice germ oil | 659 |
| Aspartic acid | 500 |
| Resveratrol | 1 |
| Lotus germ extract | 100 |
| Elastin | 180 |
| DNA | 30 |
| Folic acid | 30 |
| | 1500 |

Formulation Example 7

Granule

| (Composition) | Content (mg/pack) |
| --- | --- |
| Aspartic acid | 400 |
| Vitamin C | 100 |
| Soybean isoflavone | 250 |
| Reduced lactose | 300 |
| Soybean oligosaccharide | 36 |
| Erythritol | 36 |
| Dextrin | 30 |
| Flavoring agent | 24 |
| Citric acid | 24 |
| | 1200 |

Formulation Example 8

Beverage

| (Composition) | Content (g/60 mL) |
| --- | --- |
| *Eucommia ulmoides* extract | 1.6 |
| Ginseng extract | 1.6 |
| Aspartic acid | 0.25 |
| Reduced maltose syrup | 28 |
| Erythritol | 8 |
| Citric acid | 2 |
| Flavoring agent | 1.3 |
| N-Acetylglucosamine | 1 |
| Sodium hyaluronate | 0.5 |
| Vitamin E | 0.3 |
| Vitamin B6 | 0.2 |
| Vitamin B2 | 0.1 |
| α (alpha)-Lipoic acid | 0.2 |
| Coenzyme Q10 | 1.2 |
| Ceramide (*Konjac* extract) | 0.4 |
| L-Proline | 2 |
| Purified water | Remainder |
| | 60 |

Formulation Example 9

Candy

| (Composition) | Content (% by weight) |
| --- | --- |
| Sugar | 50 |
| Syrup | 48 |
| Aspartic acid | 1 |
| Flavoring agent | 1 |
| | 100 |

Formulation Example 10

Cookie

| (Composition) | Content (% by weight) |
| --- | --- |
| Weak flour | 45.0 |
| Butter | 17.5 |
| Granulated sugar | 20.0 |
| Aspartic acid | 4.0 |
| Egg | 12.5 |
| Flavoring agent | 1.0 |
| | 100.0 |

Method for Producing Formulation Example 10 (Cookie)

Granulated sugar is added in portions to butter while stirring, to which an egg, aspartic acid and a flavoring agent are added and stirred. After mixing thoroughly, uniformly sieved weak flour is added and stirred at a low speed, and allowed to stand as a bulk in a refrigerator. Thereafter, it is molded and baked for 15 minutes at 170° C. (degrees Celsius) to obtain a cookie.

Formulation Example 11

Bean Paste

| (Composition) | Content (g) |
| --- | --- |
| Soybean | 1000 |
| Malted rice | 1000 |
| Salt | 420 |
| Aspartic acid | 16.8 |
| Water | Remainder |
| | 4000 |

Method for Producing Formulation Example 11 (Bean Paste)

Malted rice is mixed thoroughly with a salt. Washed soybeans are soaked overnight in three times its volumes of water, which are then drained off, and new water is added while boiling, and poured into a colander to collect the broth (tanemizu fluid), to which aspartic acid is dissolved at 10% w/v. The boiled beans are minced immediately, combined with malted rice mixed with salt, to which the tanemizu fluid containing aspartic acid dissolved therein is added and kneaded evenly to obtain a clay-like hardness. Dumplings are made and stuffed in a container compactly without forming any voids, and the surface of the content is smoothened and sealed with a plastic film. After three months, the content is transferred to a new container and the surface is smoothened and sealed with a plastic film. Instead of adding aspartic acid to the tanemizu fluid, a malted rice producing a large amount of aspartic acid may be employed. Such malted rice can be selected by quantifying aspartic acid by the method described in Japanese Patent Unexamined Publication No. 2008-185558. Alternatively, a commercially available bean paste can be supplemented with aspartic acid or a salt thereof.

Formulation Example 12

French Dressing

| (Composition) | Content (g) |
|---|---|
| Salad oil | 27.4 |
| Vinegar | 30.4 |
| Sodium chloride | 0.9 |
| Aspartic acid | 0.30 |
| Pepper | 1.0 |
| | 60.0 |

Method for Producing Formulation Example 12 (French Dressing)

Vinegar is combined with sodium chloride and aspartic acid, and then stirred thoroughly to be dissolved. Salad oil is added to the mixture and the mixture is stirred thoroughly and then pepper is added.

Formulation Example 13

Mayonnaise

| (Composition) | Content (g) |
|---|---|
| Salad oil | 134.0 |
| Vinegar | 5.5 |
| Sodium chloride | 0.9 |
| Aspartic acid | 0.5 |
| Egg yolk | 18 |
| Sugar | 0.2 |
| Pepper | 0.9 |
| | 160.0 |

Method for Producing Formulation Example 13 (Mayonnaise)

An egg yolk (room temperature) is combined with vinegar, sodium chloride, aspartic acid and pepper, and stirred thoroughly using a whipping apparatus. Stirring is continued while adding salad oil in portions to form an emulsion. Finally, sugar is added and the mixture is stirred.

Formulation Example 14

French Bread

| (Composition) | Content (g) |
|---|---|
| Hard flour | 140 |
| Weak flour | 60 |
| Sodium chloride | 3 |
| Sugar | 6 |

-continued

| (Composition) | Content (g) |
|---|---|
| Aspartic acid | 2 |
| Dry yeast | 4 |
| Lukewarm water | 128 |
| | 343 |

Method for Producing Formulation Example 14 (French Bread)

Lukewarm water is combined with 1 g of sugar and dry yeast, which is then allowed to undergo a pre-fermentation. Hard flour, weak flour, sodium chloride, 5 g of sugar and aspartic acid are placed in a bowl, into which the pre-fermented yeast is placed. After kneading thoroughly into a ball-like dough, a primary fermentation is conducted at 30° C. (degrees Celsius). The dough is kneaded again and allowed to stand, and then shaped into suitable forms, which are subjected to a final fermentation using an electronic fermentation machine. After forming coupes, baking is conducted for 30 minutes in an oven at 220° C. (degrees Celsius).

Formulation Example 15

Soy Sauce

| (Composition) | Content (g) |
|---|---|
| Commercially available soy sauce | 995.8 |
| Aspartic acid | 4.2 |
| | 1000 |

Method for Producing Formulation Example 15 (Soy Sauce)

Commercially available soy sauce is supplemented with aspartic acid, and stirred thoroughly. Instead of adding aspartic acid or a salt thereof, malted rice producing a large amount of aspartic acid may be employed for fermenting soy sauce. Such malted rice can be selected by quantifying aspartic acid by the method described in Japanese Patent Unexamined Publication No. 2008-185558. Further, aspartic acid or a salt thereof may be added to commercially available soy sauce.

Formulation Example 16

Yogurt

| (Composition) | Content (g) |
|---|---|
| Milk | 880 |
| L. bulgaricus | 50 |
| S. thermophilus | 50 |
| Aspartic acid | 20 |
| | 1000 |

Method for Producing Formulation Example 16 (Yogurt)

Fermentation is conducted at 40 to 45° C. (degrees Celsius). Other commercially available fermentation seed organisms may be employed and commercially available yogurt may be supplemented with aspartic acid. Instead of adding aspartic acid or a salt thereof, a seed organism producing a large amount of aspartic acid may be employed. Such an organism can be selected by quantifying aspartic acid by the method described in Japanese Patent Unexamined Publication No. 2008-185558. Further, aspartic acid or a salt thereof may be added to commercially available yogurt.

Formulation Example 17

Dried Seasoning Powder for Rice

| (Composition) | Content (g) |
|---|---|
| Aspartic acid | 50 |
| Laver | 15 |
| Sodium L-glutamate | 10 |
| Sodium chloride | 2 |
| Roasted sesame | 10 |
| Dried mackerel shavings | 10 |
| Sugar | 1 |
| Soy sauce | 2 |
| | 100 |

Formulation Example 18

Seasoning, Sauce for Natto

| (Composition) | Content (g) |
|---|---|
| Commercially available sauce for natto | 9.96 |
| Aspartic acid | 0.04 |
| | 10 |

Formulation Example 19

Natto

| (Composition) | Content (g) |
|---|---|
| Commercially available natto | 19.9 |
| Aspartic acid | 0.1 |
| | 20 |

Method for Producing Formulation Example 19 (Natto)

Instead of adding aspartic acid or a salt thereof, an organism producing a large amount of aspartic acid may be employed for producing natto. Such an organism can be selected by quantifying aspartic acid by the method described in Japanese Patent Unexamined Publication No. 2008-185558. Further, aspartic acid or a salt thereof may be added to commercially available natto.

Formulation Example 20

Unrefined Black Vinegar

| (Composition) | Content (g) |
|---|---|
| Commercially available unrefined black vinegar | 995.8 |
| Aspartic acid | 4.2 |
| | 1000 |

Method for Producing Formulation Example 20 (Unrefined Black Vinegar)

Instead of adding aspartic acid or a salt thereof, an organism producing a large amount of aspartic acid may be employed for producing vinegar, black vinegar or unrefined vinegar. Such an organism can be selected by quantifying aspartic acid by the method described in Japanese Patent Unexamined Publication No. 2008-185558. Further, aspartic acid or a salt thereof may be added to commercially available unrefined black vinegar.

Formulation Example 21

Cream

| (Composition) | Content (%) |
|---|---|
| Liquid paraffin | 3 |
| White petrolatum | 1 |
| Dimethyl polysiloxane | 1 |
| Stearyl alcohol | 1.8 |
| Behenyl alcohol | 1.6 |
| Glycerin | 8 |
| Dipropylene glycol | 5 |
| Macadamia nut oil | 2 |
| Hydrogenated oil | 3 |
| Squalane | 6 |
| Stearic acid | 2 |
| Cholesteryl hydroxystearate | 0.5 |
| Cetyl 2-ethylhexanoate | 4 |
| Polyoxyethylene hydrogenated castor oil | 0.5 |
| Self-emulsifying glyceryl monostearate | 3 |
| Potassium hydroxide | 0.15 |
| Sodium hexametaphosphate | 0.05 |
| Trimethyl glycine | 2 |
| Potassium ascorbyl tocopheryl phosphate | 1 |
| Tocopheryl acetate | 0.1 |
| Aspartic acid | 0.42 |
| Paraben | Proper quantity |
| Edetate trisodium | 0.05 |
| 4-t-Butyl-4'-methoxy dibenzoylmethane | 0.05 |
| Glyceryl ethylhexanoate dimethoxycinnamate | 0.05 |
| Colorant | Proper quantity |
| Carboxyvinyl polymer | 0.05 |
| Purified water | Remainder |
| | 100.00 |

Formulation Example 22

Body Cream

| (Composition) | Content (%) |
| --- | --- |
| Dimethyl polysiloxane | 3 |
| Decamethyl cyclopentasiloxane | 13 |
| Dodecamethyl cyclohexasiloxane | 12 |
| Polyoxyethylene methylpolysiloxane copolymer | 1 |
| Ethanol | 2 |
| Isopropanol | 1 |
| Glycerin | 3 |
| Dipropylene glycol | 5 |
| Polyethylene glycol 6000 | 5 |
| Sodium hexametaphosphate | 0.05 |
| Tocopherol acetate | 0.1 |
| Aspartic acid | 0.3 |
| *Foeniculum vulgare* (Fennel) extract | 0.1 |
| *Hamamelis virginiana* (Witch Hazel) extract | 0.1 |
| Ginseng extract | 0.1 |
| L-Menthol | Proper quantity |
| Paraoxybenzoic acid ester (Paraben) | Proper quantity |
| Edetate trisodium | 0.05 |
| Dimorpholinopyridazinone | 0.01 |
| Isopentyl trimethoxycinnamate trisiloxane | 0.1 |
| Iron oxide yellow | Proper quantity |
| Cobalt titanium oxide | Proper quantity |
| Dimethyl distearyl ammonium hectorite | 1.5 |
| Polyvinyl alcohol | 0.1 |
| Hydroxyethylcellulose | 0.1 |
| Trimethylsiloxysilicate | 2 |
| Flavoring agent | Proper quantity |
| Purified water | Remainder |
| | 100.00 |

Formulation Example 23

Gel

| (Composition) | Content (%) |
| --- | --- |
| Dimethyl polysiloxane | 5 |
| Glycerin | 2 |
| 1,3-Butylene glycol | 5 |
| Polyethylene glycol 1500 | 3 |
| Polyethylene glycol 20000 | 3 |
| Cetyl ethylhexanoate | 3 |
| Citric acid | 0.01 |
| Sodium citrate | 0.1 |
| Sodium hexametaphosphate | 0.1 |
| Dipotassium glycyrrhizate | 0.1 |
| Aspartic acid | 0.4 |
| Tocopheryl acetate | 0.1 |
| *Scutellaria Baicalensis* root extract | 0.1 |
| *Saxifraga sarmentos* extract | 0.1 |
| Edetate trisodium | 0.1 |
| Xanthan gum | 0.3 |
| Acrylates/C10-30 alkyl acrylate crosspolymer (Pemulen TR-2) | 0.05 |

| (Composition) | Content (%) |
| --- | --- |
| Agar powder | 1.5 |
| Phenoxyethanol | Proper quantity |
| Dibutylhydroxytoluene | Proper quantity |
| Purified water | Remainder |
| | 100.00 |

Formulation Example 24

Peel-Off Mask

| (Composition) | Content (%) |
| --- | --- |
| Ethanol | 10 |
| 1,3-Butylene glycol | 6 |
| Polyethylene glycol 4000 | 2 |
| Olive oil | 1 |
| Macadamia nut oil | 1 |
| Phytosteryl hydroxystearic acid | 0.05 |
| Lactic acid | 0.05 |
| Sodium lactate | 0.1 |
| Disodium ascorbyl sulfate | 0.1 |
| Potassium ascorbyl tocopheryl phosphate | 0.1 |
| Aspartic acid | 0.3 |
| Fish collagen | 0.1 |
| Sodium chondroitin sulfate | 0.1 |
| Sodium carboxymethyl cellulose | 0.2 |
| Polyvinyl alcohol | 12 |
| Paraoxybenzoic acid ester (Paraben) | Proper quantity |
| Flavoring agent | Proper quantity |
| Purified water | Remainder |
| | 100.00 |

Formulation Example 25

Wet Pack

| (Composition) | Content (%) |
| --- | --- |
| Glycerin | 1 |
| 1,3-Butylene glycol | 8 |
| Xylit | 2 |
| Polyethylene glycol 1500 | 2 |
| Rosemary oil | 0.01 |
| Sage oil | 0.1 |
| Citric acid | 0.02 |
| Sodium citrate | 0.08 |
| Sodium hexametaphosphate | 0.01 |
| Hydroxypropyl-β(beta)-cyclodextrin | 0.1 |
| Aspartic acid | 0.2 |
| Birch extract | 0.1 |
| Lavender oil | 0.01 |
| Xanthane gum | 0.05 |
| Carboxylvinyl polymer | 0.15 |
| Paraoxybenzoic acid ester (Paraben) | Proper quantity |
| Purified water | Remainder |
| | 100.00 |

Formulation Example 26

Emulsion

| (Composition) | Content (%) |
|---|---|
| Liquid paraffin | 7 |
| White petrolatum | 3 |
| Decamethyl cyclopentasiloxane | 2 |
| Behenyl alcohol | 1.5 |
| Glycerin | 5 |
| Dipropylene glycol | 7 |
| Polyethylene glycol 1500 | 2 |
| Jojoba oil | 1 |
| Isostearic acid | 0.5 |
| Stearic acid | 0.5 |
| Behenic acid | 0.5 |
| Pentaerythritol tetra (2-ethylhexanoate) | 3 |
| Cetyl 2-ethylhexanoate | 3 |
| Glycerin monostearate | 1 |
| Polyoxyethylene-glycerin monostearate | 1 |
| Potassium hydroxide | 0.1 |
| Sodium hexametaphosphate | 0.05 |
| Stearyl glycyrrhetinate | 0.05 |
| Aspartic acid | 0.3 |
| Royal jelly extract | 0.1 |
| Yeast extract | 0.1 |
| Tocopherol acetate | 0.1 |
| Acetylated sodium hyaluronate | 0.1 |
| Edetate trisodium | 0.05 |
| 4-t-Butyl-4'-methoxydibenzoyl methane | 0.1 |
| 2-Ethylhexyl paramethoxycinnamate | 0.1 |
| Carboxylvinyl polymer | 0.15 |
| Paraben | Proper quantity |
| Flavoring agent | Proper quantity |
| Purified water | Remainder |
| | 100.00 |

Formulation Example 27

Emulsion

| (Composition) | Content (%) |
|---|---|
| Dimethylpolysiloxane | 2 |
| Behenyl alcohol | 1 |
| Batyl alcohol | 0.5 |
| Glycerin | 5 |
| 1,3-Butylene glycol | 7 |
| Erythritol | 2 |
| Hydrogenated oil | 3 |
| Squalane | 6 |
| Pentaerythritol tetra (2-ethylhexanoate) | 2 |
| Polyoxyethylene glyceryl isostearate | 1 |
| Polyoxyethylene glyceryl monostearate | 1 |
| Aspartic acid | 0.3 |
| Potassium hydroxide | Proper quantity |
| Sodium hexametaphosphate | 0.05 |
| Phenoxyethanol | Proper quantity |
| Carboxylvinyl polymer | 0.1 |
| Purified water | Remainder |
| | 100.00 |

Formulation Example 28

Skin Lotion

| (Composition) | Content (%) |
|---|---|
| Ethyl alcohol | 5 |
| Glycerin | 1 |
| 1,3-Butylene glycol | 5 |
| Polyoxyethylene-polyoxypropylene decyltetradecyl ether | 0.2 |
| Sodium hexametaphosphate | 0.03 |
| Trimethyl glycine | 1 |
| Sodium polyasparaginate | 0.1 |
| Potassium ascorbyl tocopheryl phosphate | 0.1 |
| Thiotaurine | 0.1 |
| Aspartic acid | 0.2 |
| Edetate trisodium | 0.1 |
| Carboxylvinyl polymer | 0.05 |
| Potassium hydroxide | 0.02 |
| Phenoxyethanol | Proper quantity |
| Flavoring agent | Proper quantity |
| Purified water | Remainder |
| | 100.00 |

Formulation Example 29

Skin Lotion

| (Composition) | Content (%) |
|---|---|
| Ethanol | 10 |
| Dipropylene glycol | 1 |
| Polyethylene glycol 1000 | 1 |
| Polyoxyethylene methyl glucoside | 1 |
| Jojoba oil | 0.01 |
| Glyceryl tri(2-ethylhexanoate) | 0.1 |
| Polyoxyethylene hydrogenated castor oil | 0.2 |
| Polyglyceryl diisostearate | 0.15 |
| Sodium N-stearoyl-L-glutamate | 0.1 |
| Citric acid | 0.05 |
| Sodium citrate | 0.2 |
| Potassium hydroxide | 0.4 |
| Dipotassium glycyrrhizate | 0.1 |
| Arginine hydrochloride | 0.1 |
| L-Ascorbic acid 2-glucoside | 2 |
| Aspartic acid | 0.2 |
| Edetate trisodium | 0.05 |
| Octyl 4-methoxycinnamate | 0.01 |

-continued

| (Composition) | Content (%) |
|---|---|
| Dibutylhydroxytoluene | Proper quantity |
| Paraben | Proper quantity |
| Deep sea water | 3 |
| Flavoring agent | Proper quantity |
| Purified water | Remainder |
| | 100.00 |

Formulation Example 30

Stock Solution of Aerosol Urea Preparation for External Use

| (Composition) | Content (% by weight) |
|---|---|
| Ethanol | 15.0 |
| Polyoxyethylene hydrogenated castor oil 50 | 1.5 |
| Diphenhydramine | 1.0 |
| Dibucaine | 2.0 |
| Tocopheryl acetate | 0.5 |
| Aspartic acid | 0.1 |
| Isostearic acid | 0.1 |
| 1,3-Butylene glycol | 3.0 |
| Polyethylene glycol 400 | 3.0 |
| Camphor | 0.05 |
| Urea | 20.0 |
| Purified water | Remainder |
| | 100.00 |

Formulation Example 31

Aerosol Urea Spray

| (Composition) | Content (% by weight) |
|---|---|
| Stock solution of aerosol urea preparation for external use | 65.0 |
| Dimethyl ether | 35.0 |
| | 100.00 |

Method of Filling Formulation Example 31 (Aerosol Urea Spray)

Stock solution of an aerosol urea external preparation and dimethyl ether are filled in a pressure resistant aerosol aluminum can of which internal surface is coated with Teflon (registered trade mark) to prepare an aerosol preparation.

The invention claimed is:

1. A method of improving a skin condition associated with oxidative damage comprising administering to a subject in need thereof, an antioxidant composition consisting essentially of D-aspartic acid and/or salts thereof.

2. The method of claim 1, wherein the skin condition comprises fine wrinkles, a rough skin, a dry skin, a skin cancer, a skin allergy, an inflammation of the skin, and a photosensitive dermatosis.

3. The method of claim 1, wherein the antioxidant composition is used for an external preparation for the skin.

4. The method of claim 1, wherein the antioxidant composition is used for a food composition.

5. The method of claim 1, wherein the content of the D-aspartic acid and/or salt thereof is between about 0.0003% by weight of the composition to about 3% by weight of the composition.

* * * * *